(12) United States Patent
McDonnell et al.

(10) Patent No.: US 8,409,501 B2
(45) Date of Patent: Apr. 2, 2013

(54) METHOD OF DEACTIVATING CONTAMINANTS IN A REGION USING A MOBILE DEACTIVATION APPARATUS

(75) Inventors: Gerald E. McDonnell, Basingstoke (GB); Thaddeus J. Mielnik, Concord, OH (US); Francis J. Zelina, Lake City, PA (US); Michael A. Centanni, Parma, OH (US)

(73) Assignee: American Sterilizer Company, Mentor, OH (US)

( * ) Notice: Subject to any disclaimer, the term of this patent is extended or adjusted under 35 U.S.C. 154(b) by 360 days.

(21) Appl. No.: 12/938,863

(22) Filed: Nov. 3, 2010

(65) Prior Publication Data

US 2011/0058981 A1    Mar. 10, 2011

Related U.S. Application Data

(62) Division of application No. 11/201,474, filed on Aug. 11, 2005, now Pat. No. 7,850,931.

(51) Int. Cl.
| | |
|---|---|
| *A61L 2/00* | (2006.01) |
| *A61L 2/18* | (2006.01) |
| *A61L 9/00* | (2006.01) |
| A61L 2/04 | (2006.01) |
| A61L 11/00 | (2006.01) |
| A61L 2/24 | (2006.01) |
| C23F 11/00 | (2006.01) |
| F01N 3/20 | (2006.01) |
| G05B 1/00 | (2006.01) |

(52) U.S. Cl. ............... 422/28; 422/29; 422/1; 422/3; 422/105; 422/108; 422/243; 422/291; 422/292

(58) Field of Classification Search ............ 422/28, 422/29, 1, 3, 105, 108, 243, 291, 292
See application file for complete search history.

(56) References Cited

U.S. PATENT DOCUMENTS

| 1,527,224 A | 2/1925 | Riordan ............... 422/124 |
| 4,241,020 A | 12/1980 | Grantham ............. 422/109 |
| 4,688,585 A | 8/1987 | Vetter ................... 134/56 R |

(Continued)

FOREIGN PATENT DOCUMENTS

| EP | 1 500 404 | 1/2005 |
| EP | 1 695 652 | 8/2006 |

(Continued)

OTHER PUBLICATIONS

International Search Report and Written Opinion for International Application No. PCT/US06/27403, Jan. 24, 2007.

(Continued)

*Primary Examiner* — Regina M Yoo
(74) *Attorney, Agent, or Firm* — Kusner & Jaffe; Michael A. Centanni (57) ABSTRACT

A mobile deactivation apparatus for deactivating contaminants within a defined region that includes a source of a vaporous deactivating agent, a gas handling system, a support member, a drive means, a control system, and a power system is disclosed. The gas handling system dispenses the vaporous deactivating agent to the defined region. The support member is movable in the defined region and supports the source of the vaporous deactivating agent and the gas handling system. The support member can be propelled by the drive means. The control system is programmed to control the operation of the gas handling system and the drive means. A power system is provided to supply power to the mobile deactivation apparatus.

18 Claims, 3 Drawing Sheets

U.S. PATENT DOCUMENTS

| | | | |
|---|---|---|---|
| 4,956,145 A | 9/1990 | Cummings et al. | 422/28 |
| 5,173,258 A | 12/1992 | Childers | 422/27 |
| 5,364,590 A | 11/1994 | Hillebrenner | 422/28 |
| 5,387,403 A | 2/1995 | Ikeuchi et al. | 422/292 |
| 5,389,336 A | 2/1995 | Childers | 422/28 |
| 5,445,792 A | 8/1995 | Rickloff et al. | 422/28 |
| 5,460,845 A | 10/1995 | Dalmasso et al. | 426/320 |
| 5,534,221 A | 7/1996 | Hillebrenner et al. | 422/33 |
| 5,535,667 A | 7/1996 | Dalmasso et al. | 99/472 |
| 5,556,607 A | 9/1996 | Childers et al. | 422/300 |
| 5,815,880 A | 10/1998 | Nakanishi | 15/319 |
| 5,869,910 A | 2/1999 | Colens | 307/104 |
| 5,876,664 A | 3/1999 | Childers et al. | 422/28 |
| 6,459,955 B1 | 10/2002 | Bartsch et al. | 700/245 |
| 6,555,053 B1 | 4/2003 | Aoyagi | 422/5 |
| 6,620,380 B2 | 9/2003 | Thomas et al. | 422/29 |
| 2001/0004719 A1 | 6/2001 | Sommer | 701/23 |
| 2003/0035764 A1 | 2/2003 | Thomas et al. | 422/186.07 |
| 2003/0133834 A1 | 7/2003 | Karle | 422/33 |
| 2004/0022673 A1 | 2/2004 | Protic | 422/28 |
| 2004/0215046 A1 | 10/2004 | McVey et al. | 588/200 |
| 2005/0022330 A1 | 2/2005 | Park et al. | 15/319 |
| 2005/0031486 A1 | 2/2005 | Mole et al. | 422/32 |
| 2005/0074359 A1 | 4/2005 | Krieger et al. | 422/28 |
| 2006/0008379 A1 | 1/2006 | Mielnik et al. | 422/32 |
| 2006/0241549 A1 | 10/2006 | Sunnen | 604/23 |
| 2007/0041008 A1 | 2/2007 | Aufmuth et al. | 356/237.2 |
| 2008/0206092 A1 | 8/2008 | Crapser et al. | 422/5 |

FOREIGN PATENT DOCUMENTS

| | | |
|---|---|---|
| WO | WO 02/079818 | 10/2002 |
| WO | WO 03/082355 | 10/2003 |
| WO | WO 2004/097350 | 11/2004 |
| WO | WO 2005/033682 | 4/2005 |
| WO | WO 2007/008205 | 1/2007 |

OTHER PUBLICATIONS

Extended European Search Report for European Patent Application No. EP 06787327.3, Jun. 9, 2010.

METHOD OF DEACTIVATING CONTAMINANTS IN A REGION USING A MOBILE DEACTIVATION APPARATUS

RELATED APPLICATIONS

This application is a divisional of U.S. application Ser. No. 11/201,474, filed Aug. 11, 2005 now U.S. Pat. No. 7,850,931 which is fully incorporated herein by reference.

FIELD OF THE INVENTION

The present invention relates generally to the art of deactivation of contaminants, and more particularly to a deactivation method and apparatus that provides a vaporous deactivating agent to a region from a mobile, self-contained device.

BACKGROUND OF THE INVENTION

Deactivation of biological and chemical contaminants within rooms may be required for a number of reasons. It is known to use temporary deactivation systems to deactivate biological and chemical contaminants in rooms that do not have permanent deactivation systems. Such rooms include hotel rooms, offices, warehouses, laboratories, and the like.

Known temporary systems for the deactivation of biological and chemical contaminants within rooms utilize gaseous or vaporous deactivating agents, such as vaporized hydrogen peroxide, ozone, and chlorine-containing compounds. These deactivating agents can be hazardous to humans and are distributed using a system of ducts, fans, and hoses.

One problem with known systems is that human operators must wear protective clothing during operation of the systems. Another problem with known systems is that the system of ducts, fans, and hoses may not adequately distribute a vaporous deactivating agent throughout a room, especially rooms that are large or complexly shaped.

The present invention overcomes these and other problems, and provides a method and apparatus for the deactivation of biological and chemical contaminants within a room using a mobile, self-contained device.

SUMMARY OF THE INVENTION

In accordance with the present invention, there is provided a mobile deactivation apparatus for deactivating contaminants within a defined region that comprises: A) a source of a vaporous deactivating agent, B) a gas handling system for dispensing the vaporous deactivating agent to the defined region, C) a support member movable in the defined region, wherein the support member supports the source of the vaporous deactivating agent and the gas handling system, D) drive means for propelling the support member, E) a control system that is programmed to control the operation of the gas handling system and the drive means, and F) a power system for supplying power to the mobile deactivation apparatus.

In accordance with another aspect of the present invention, there is provided a method of deactivating contaminants within a defined region using a self-contained mobile deactivation apparatus. The apparatus includes a dimensional sensor, a system controller, and a system operable to provide and dispense a vaporous deactivating agent from the self-contained mobile deactivation apparatus. The method includes the steps of: A) determining at least one region parameter associated with said defined region, B) determining at least one operating parameter in accordance with said at least one region parameter associated with said defined region, and C) deactivating at least a portion of said defined region in accordance with said at least one operating parameter.

In yet another aspect of the present invention, a system controller is provided that is programmed to store data regarding the movements and locations of a self-contained, mobile deactivation apparatus within a defined region. The system controller uses the stored data to determine operating parameters of the self-contained, mobile deactivation apparatus such that it is operable to effectively distribute a vaporous deactivating agent throughout a large or complexly shaped defined region. LOOM An advantage of the present invention is that it provides a deactivation apparatus that is mobile and self-contained.

Another advantage of the present invention is an apparatus as defined above that can deactivate contaminants in a defined region without the presence of human operators within the defined region.

Another advantage of the present invention is an apparatus as defined above that can utilize vaporized hydrogen peroxide to deactivate contaminants in the defined region.

A further advantage of the present invention is an apparatus as defined above that is operable to determine an effective deactivation cycle.

A further advantage of the present invention is an apparatus as defined above that is operable to determine an effective deactivation cycle based on sensed data.

A still further advantage of the present invention is an apparatus as defined above that is operable to move about a defined region.

A still further advantage of the present invention is an apparatus as defined above that is operable to sense the dimensions of a defined region.

A still further advantage of the present invention is an apparatus as defined above that is operable to effectively deactivate contaminants in a defined region by moving about the defined region.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

As used herein, the term "deactivation" includes, but is not limited to, "sterilization," "disinfection," and "decontamination" processes. The term "contaminants" as used herein includes, but is not limited to, biological and chemical contaminants. The term "deactivating agent" refers herein to a chemical agent that deactivates contaminants.

Figure 1:
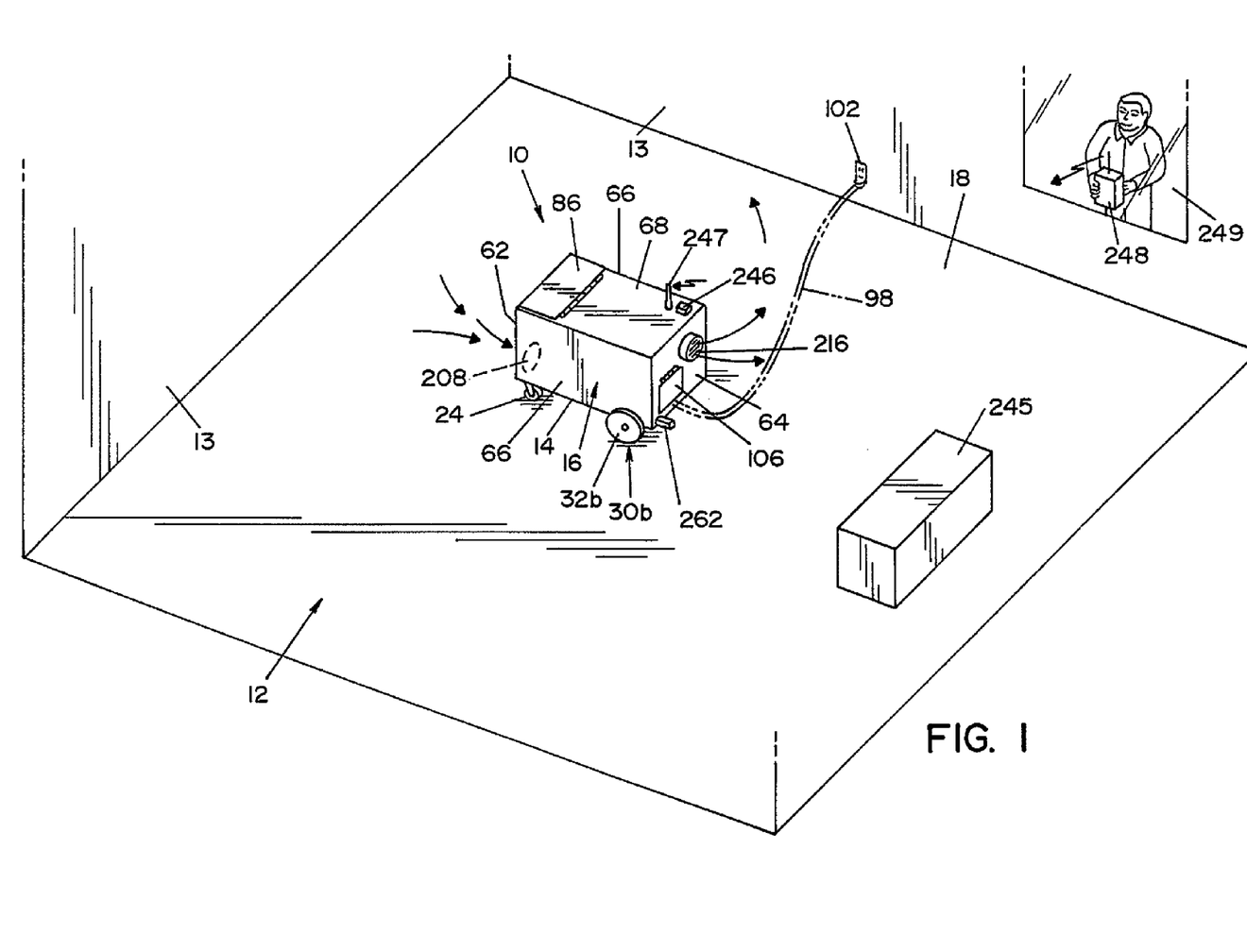
FIG. 1 is a perspective view of a preferred embodiment of a mobile deactivation apparatus disposed in a defined region in which contaminants are to be deactivated.

Referring now to the drawings wherein the showings are for the purpose of illustrating a preferred embodiment of the invention only, and not for the purpose of limiting same, FIG. 1 shows a mobile deactivation apparatus 10, illustrating a preferred embodiment of the present invention.

Broadly stated, apparatus 10 provides a mobile deactivation unit for using a vaporous deactivating agent to deactivate contaminants in a defined region 12 bordered by a plurality of walls 13 and a floor 18. By way of example and not limitation, defined region 12 may be one of: a hotel room, a clean room, a laboratory, an office, a manufacturing facility, a warehouse, or the like.

Figure 2:
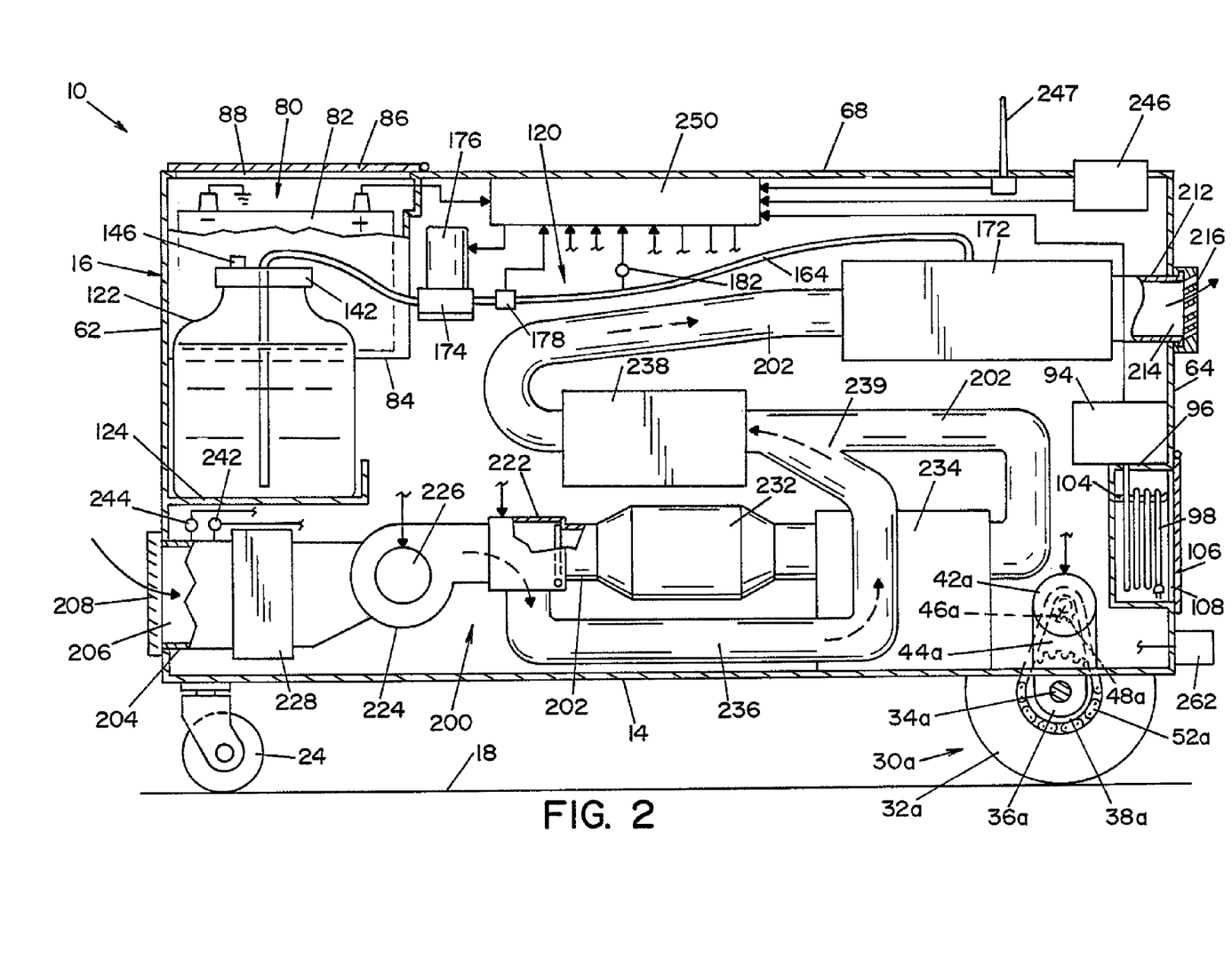
FIG. 2 is a side sectional view of the mobile deactivation apparatus of FIG. 1, according to a preferred embodiment of the present invention.
Figure 3:
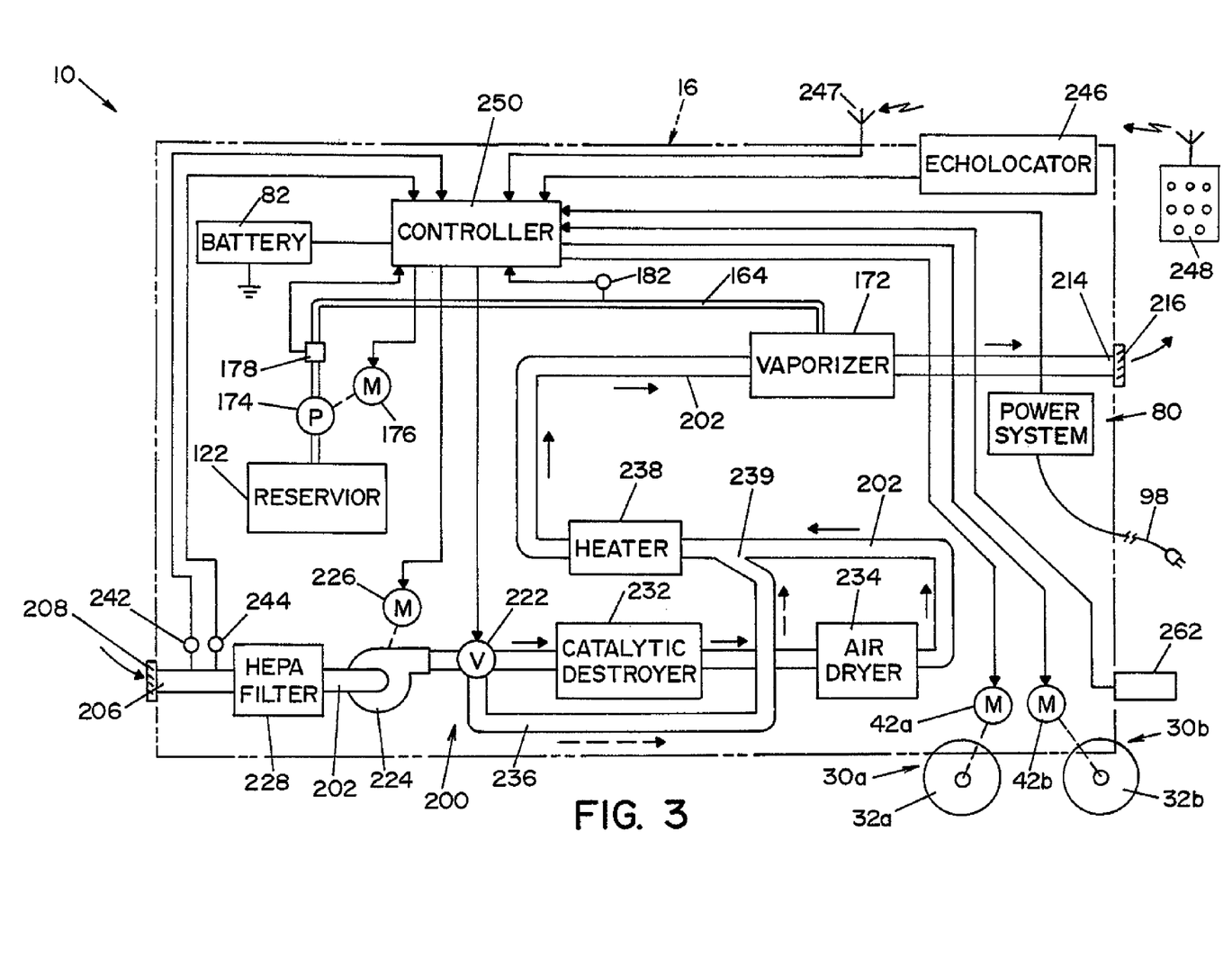
FIG. 3 is a block diagram of the mobile deactivation apparatus of FIG. 1, according to a preferred embodiment of the present invention.

Referring now to FIGS. 1-3, apparatus 10 includes a chassis 14 and a housing 16. Chassis 14 acts as a support member to support housing 16. Housing 16 has a first end wall 62, a second end wall 64, two side walls 66, and a top wall 68. By way of example and not limitation, chassis 14 and housing 16 are formed of at least one of the following: a metal (e.g., steel or aluminum), a polymer material (e.g., plastic or fiberglass), a composite material, or a combination thereof.

Apparatus 10 also includes a first drive mechanism 30a, a second drive mechanism 30b (not shown in its entirety), a power system 80, a deactivating agent supply system 120, a gas handling system 200, and a system controller 250, that are contained within, and supported by, housing 16 and chassis 14.

At least one caster 24 and drive mechanisms 30a, 30b are mounted on chassis 14 to facilitate movement of apparatus 10 on floor 18, as will be described in detail below. In the illustrated embodiment, the at least one caster 24 and drive mechanisms 30a, 30b are located at opposite ends of chassis 14.

Drive mechanisms 30a, 30b are located on opposite sides of chassis 14, and are operable to propel apparatus 10 as will be described further below. The pair of drive mechanisms 30a, 30b are substantially similar and accordingly, only first drive mechanism 30a is shown and described in detail. Like components of drive mechanisms 30a and 30b are designated with like numbers.

With regard to the illustrated embodiment of drive mechanism 30a, an axle 34a is coupled to chassis 14 by a bracket 36a. A drive wheel 32a is mounted on axle 34a. Axle 34a also has a driven sprocket 38a fixed thereon. A drive motor 42a is coupled to chassis 14 by a mount 44a. Motor 42a has a drive shaft 46a extending therefrom. A drive sprocket 48a is fixed on drive shaft 46a. A flexible, continuous drive member 52a extends around and between driven sprocket 38a and drive sprocket 48a. In a preferred embodiment, drive member 52a is a drive chain. Drive sprocket 48a, drive member 52a, and driven sprocket 38a comprise a drive coupling means. It is appreciated that the drive coupling means could be any suitable power transmission system known in the art.

As will be discussed further below, system controller 250 controls the operation of drive motors 42a, 42b. Drive motor 42a rotates drive shaft 46a. When drive shaft 46a is rotated, drive sprocket 48a turns and causes drive member 52a to transfer power to driven sprocket 38a and hence to wheel 32a. When drive motors 42a, 42b are operated at different speeds, apparatus 10 changes direction. In this manner, the speed and direction of travel of apparatus 10 can be varied. Drive mechanisms 30a, 30b, together with system controller 250, comprise a drive system that provides self-propulsion of chassis 14, and hence apparatus 10.

Referring now to FIGS. 1 and 2, power system 80 includes a battery 82 for providing electrical energy to apparatus 10. In the illustrated embodiment, battery 82 is supported on a platform 84 attached to housing 16. An external power source 102 can also provide electrical energy to apparatus 10 via a transformer 94. A shelf 96 for supporting transformer 94 is attached to housing 16. Power source 102 can be used to recharge battery 82 or provide power directly to components of apparatus 10 when electrically connected to transformer 94 by a power cord 98. In the illustrated embodiment, power cord 98 is stored on a hanger 104 when power cord 98 is not connected to power source 102.

A first opening 88 and a second opening 108 are defined through housing 16. First opening 88 provides access to battery 82, while second opening 108 provides access to power cord 98. A first hatch 86 and a second hatch 106 are disposed such that they cover first opening 88 and second opening 108, respectively. In the illustrated embodiment, first hatch 86 and second hatch 106 preferably pivot between open and closed positions.

Deactivating agent supply system 120 includes a source for a vaporous deactivating agent. In a preferred embodiment, the source for a vaporous deactivating agent includes a means for generating a vaporous deactivating agent from a stored liquid deactivating agent and a means for storing the liquid deactivating agent. It is appreciated that in other embodiments, the source for a vaporous deactivating agent can include a container for storing a vaporous deactivating agent, a vapor generation device, or a means for storing and receiving chemical components to form a vaporous deactivating agent. As used herein, the terms "gaseous" or "gas" shall refer to gases and/or vapors, wherein vapors are generated by vaporizing liquids.

In the illustrated embodiment, deactivating agent supply system 120 includes a reservoir 122. Reservoir 122 is a means for storing liquid deactivating agent and is preferably a tank or vessel. A shelf 124 supports reservoir 122. Reservoir 122 is accessible through first opening 88 described above. Reservoir 122 includes a cap 142 that has a vent 146 formed therein. Vent 146 operates to equalize an internal pressure of reservoir 122 with a pressure external to reservoir 122, without allowing fluid to escape reservoir 122. In one embodiment, vent 146 is a check valve. By way of example and not limitation, reservoir 122 is made of at least one of the following materials: a glass, a polymer, and a ceramic.

A deactivating agent supply conduit 164 fluidly connects reservoir 122 to vaporizer 172. Vaporizer 172 vaporizes the liquid deactivating agent by conventionally known means to form the vaporous deactivating agent. A pump 174 is disposed in conduit 164 between cap 142 and vaporizer 172. Pump 174 is driven by a pump motor 176 and is provided to convey metered amounts of the liquid deactivating agent through conduit 164 to vaporizer 172.

A flow sensor 178 is disposed within conduit 164 for sensing the flow of fluids therethrough. In an alternate embodiment, flow sensor 178 may be substituted for by a balance (not shown) for determining the mass of liquid deactivating agent within reservoir 122. The balance is disposed under reservoir 122.

A liquid deactivating agent sensor 182 senses a concentration of liquid deactivating agent within conduit 164. Sensor 182 is preferably disposed within conduit 164 between cap 142 and vaporizer 172.

Gas handling system 200 is operable to transport a gas. By way of example and not limitation, the gas transported by gas handling system 200 includes one of the following: the atmosphere of the defined region, any gas or vapor generated by apparatus 10, and a combination thereof. Gas handling system 200 includes a primary conduit 202 having a first end 204 and a second end 212. First end 204 of primary conduit 202 defines an inlet 206 within first end wall 62 of housing 16. Second end 212 of conduit 202 defines an outlet 214 within second end wall 64. Primary conduit 202 is in fluid communication with defined region 12, extending between inlet 206 and outlet 214.

A first louver 208 is mounted to first end wall 62 such that it covers inlet 206. A second louver 216 is mounted to second end wall 64 such that it covers outlet 214. In the embodiment shown, first louver 208 and second louver 216 are mounted such that they have a fixed orientation and are operable to determine the direction of flow of gas into and out of primary conduit 202 and defined region 12 respectively. It is appreciated that in one embodiment, first louver 208 and second louver 216 have an adjustable orientation that is at least one of manually and automatically adjustable.

Conduit 202 defines a primary gas flow path of gas handling system 200. A blower 224 draws gas into conduit 202 through inlet 206. Vaporizer 172 is located in conduit 202 downstream from blower 224. A catalytic destroyer 232 is disposed in conduit 202 between blower 224 and vaporizer 172. Catalytic destroyer 232 is operable to destroy vaporous deactivating agent flowing therethrough, as is conventionally known. A heater 238 for heating the gas is disposed in conduit 202 between destroyer 232 and vaporizer 172. In the illustrated embodiment, a filter 228 for removing contaminants from the gas is disposed within primary conduit 202 between inlet 206 and blower 224. In one embodiment, filter 228 is a HEPA filter.

A bypass conduit 236 defines a bypass gas flow path extending between blower 224 and heater 238. A first end of bypass conduit 236 connects with a valve 222 disposed in conduit 202 between blower 224 and destroyer 232. Valve 222 is movable between a first position and a second position. In the first position gas is allowed to flow through primary conduit 202 and is prevented from flowing through bypass conduit 236. In the second position gas is prevented from flowing through primary conduit 202 and is allowed to flow through bypass conduit 236. In the illustrated embodiment, bypass conduit 236 has a second end that connects with primary conduit 202 at a junction 239 that is located proximate to the input end of heater 238. When valve 222 is in the second position, as discussed above, gas flows through bypass conduit 236 and bypasses catalytic destroyer 232 and dryer 234.

A vaporous deactivating agent sensor 242 for sensing vaporous deactivating agent and a moisture sensor 244 for sensing one of percent moisture and relative humidity are disposed within primary conduit 202 between inlet 206 and valve 222. In this manner, the moisture content and vaporous deactivating agent content of the atmosphere of defined region 12 are determined by sensing the gas drawn into conduit 202 from defined region 12 as it passes through conduit 202.

An echolocator 246 for sensing the location of walls 13 relative to apparatus 10 is preferably disposed on top wall 68. As used herein, the term "echolocator" refers to a dimensional sensor that is operable to determine the dimensions of a surrounding environment using echolocation. Echolocator 246 is operable to determine the location of boundaries of regions relative to apparatus 10 using echolocation. Echolocation is a conventionally known technique utilized in methods such as radar and sonar. By way of example and not limitation, echolocator 246 determines the dimensions of defined region 12 using at least one of the following: electromagnetic radiation (e.g., radio frequency or infrared signals) and sound waves (e.g., sonic or ultrasonic signals). In one embodiment, echolocator 246 is operable to determine the location of an object 245 that may restrict movement of apparatus 10 within defined region 12.

Flow sensor 178, liquid deactivating agent sensor 182, vaporous deactivating agent sensor 242, moisture sensor 244, and echolocator 246 comprise a sensing system. The sensing system is distributed such that the sensors can be disposed in various locations and in various configurations throughout apparatus 10. In one embodiment, the sensing system includes a first group of sensors and a second group of sensors.

The first group of sensors comprises means for sensing region parameters associated with defined region 12. By way of example and not limitation, region parameters include: dimensions associated with defined region 12 (e.g., volume, area, height, shape, layout, perimeter, and the like); a location of one or more objects disposed within defined region 12; environmental conditions associated with defined region 12 (e.g., temperature, relative humidity, moisture content, pressure, and the like); a concentration of a vaporous deactivating agent within defined region 12, and a combination thereof. In the illustrated embodiment, the first group of sensors includes vaporous deactivating agent sensor 242, moisture sensor 244, and echolocator 246.

The second group of sensors comprises means for sensing internal system parameters. By way of example and not limitation, the internal parameters include: a flow of the liquid deactivating agent, a concentration of the liquid deactivating agent, a temperature of liquid deactivating agent, and a combination thereof. The second group of sensors includes flow sensor 178 and liquid deactivating agent sensor 182.

A system controller 250 is disposed within housing 16 and is schematically illustrated in FIG. 3. In the illustrated embodiment, system controller 250 is a system microprocessor or micro-controller that is programmed to control the operation of apparatus 10 and is operable as will be described further below. As schematically illustrated in FIG. 3, controller 250 is electrically connected to pump motor 176, blower motor 226, valve 222, and drive motors 42a, 42b. System controller 250 is also electrically connected to the sensors comprising the sensing system.

Controller 250 is operable to control the direction and speed of travel of apparatus 10 by varying the relative speed of motors 42a, 42b. For example, when the speed of motors 42a, 42b is maintained such that a rate of travel of wheels 32a, 32b along floor 18 is equal, apparatus 10 travels in a straight line. When the speed of motors 42a, 42b is maintained such that the rate of travel of wheels 32a, 32b along floor 18 is unequal, apparatus 10 travels in a curve that is directed away from the faster of wheels 32a, 32b. When the speed of motors 42a, 42b is maintained such that the rate of travel of one of wheels 32a, 32b along floor 18 is zero and the rate of travel of the other of wheels 32a, 32b is greater than zero, apparatus 10 rotates about the one of wheels 32a, 32b having a zero rate of linear travel.

Controller 250 is also operable to store predetermined data sets. Controller 250 is programmed to monitor and control a desired concentration of vaporous deactivating agent based upon operating parameters. By way of example and not limitation, the operating parameters include: a desired flow of the liquid deactivating agent, a desired concentration of the liquid deactivating agent, a desired temperature of liquid deactivating agent, a desired vaporous deactivating agent concentration, a duration of a deactivation phase, whether apparatus 10 is mobile during a deactivation phase, a duration of a phase of a deactivation cycle as discussed below, and a combination thereof.

Furthermore, controller 250 is operable to receive wireless communication signals such that data may be manipulated and operation instructions may be received from a base station 248 via an antenna 247. In the illustrated embodiment antenna 247 is disposed on top wall 68. Antenna 247 is electrically connected to controller 250, and allows controller 250 to communicate with base station 248 by means of electromagnetic waves.

Base station 248 includes input means to receive operator input and is located external to defined region 12. Base station 248 is operable to provide instructions to system controller 250 regarding the operation of apparatus 10 based on stored data or based on human input. In one embodiment, also shown in FIG. 1, base station 248 is disposed such that apparatus 10 is visible to an operator from outside of defined region 12 when the operator is in a position to access base station 248. By way of example and not limitation, apparatus 10 is visible to an operator by means of at least one of: a window 249 defined in walls 13, a remote video system (not shown), or a combination thereof.

The present invention shall now be further described with reference to the operation of apparatus 10. In accordance with a preferred embodiment of the present invention, operation of apparatus 10 includes three modes that occur sequentially. A first mode includes preparing defined region 12 for deactivation. A second mode includes initializing a deactivation cycle. A third mode includes executing a deactivation cycle. As used herein, the term "deactivation cycle" refers to a series of phases that are necessary for apparatus 10 to effect the deactivation of contaminants within defined region 12 and to reduce the deactivating agent concentration to a predetermined threshold. The series of phases of a typical deactivation cycle include a drying phase, a conditioning phase, a deactivation phase, and a destroying phase. System controller 250 controls the deactivation cycle in accordance with the operating parameters discussed above.

Referring now to the first mode mentioned above, apparatus 10 is placed within defined region 12, and defined region 12 is sealed. In one embodiment, defined region 12 is sealed such that deactivating agent released within defined region 12 is maintained within defined region 12. Apparatus 10 is configured to operate within defined region 12 without human manipulation or control. Therefore, apparatus 10 is sealed within defined region 12 without any human operators present therein. After completion of the first mode, wherein defined region 12 and apparatus 10 are prepared, the second mode commences.

Referring now to the second mode, initializing a deactivation cycle is the process of determining the operating parameters. By way of example and not limitation, the operating parameters are determined by system controller 250 in accordance with at least one of: stored data sets, region parameters, input from a human operator by means of base station 248, and a combination thereof.

In the case of deactivation by vaporized hydrogen peroxide, the percentage concentration of liquid hydrogen peroxide in the liquid deactivating agent solution is determined during the second mode. In a preferred embodiment, the percentage concentration of liquid hydrogen peroxide in the liquid deactivating agent solution is provided by liquid deactivating agent sensor 182. In one embodiment, a liquid deactivating agent solution of 35% hydrogen peroxide and 65% water is used. However, other concentrations of hydrogen peroxide and water are contemplated.

In the illustrated embodiment, a region parameter is used to determine at least one of the operating parameters mentioned above. System controller 250 determines at least one of the following operating parameters in accordance with the volume of defined region 12: (a) the duration of the deactivation phase, and (b) the desired concentration of vaporous deactivating agent within the atmosphere of defined region 12. In this manner, the deactivation cycle is optimized for defined region 12 such that the desired level of deactivation is achieved within the desired length of time.

In the illustrated embodiment of the present invention, system controller 250 determines the volume of defined region 12 using the equation V=HA, where V is the volume of defined region 12, H is a height of defined region 12, and A is an area of floor 18 of defined region 12. System controller 250 determines the height H by reference to a stored data set. The area, A, is determined in two stages: first, echolocator 246 senses walls 13 and provides data to controller 250 that is indicative of the location of the walls 13 relative to apparatus 10. Second, controller 250 determines the area, A, using data provided by echolocator 246 and predetermined, algorithms.

In another embodiment of the present invention, echolocator 246 is operable to provide data to system controller 250 that is indicative of the height, H, of defined region 12.

System controller 250 is also operable to determine whether apparatus 10 can adequately deactivate contaminants within defined region 12 by remaining stationary during the deactivation cycle, or whether it will be necessary for apparatus 10 to be mobile during the deactivation cycle. To determine whether apparatus 10 can remain stationary or if mobility is necessary, controller 250 is operable to compare the volume, V, of defined region 12 to a predetermined maximum volume, $V_{max}$. Accordingly, if V is less than or equal to $V_{max}$, apparatus 10 can remain stationary during a deactivation cycle, whereas if V is greater than $V_{max}$, apparatus 10 will need to be mobile during the deactivation cycle. A "mobile" deactivation cycle will be discussed further below.

Referring now to a typical deactivation cycle of the illustrated embodiment, system controller 250 operates during a deactivation cycle to monitor and control the desired concentrations of vaporous deactivating agent in accordance with at least one of the operating parameters. The operating parameters used include the desired vaporous deactivating agent concentration, a duration of time during which vaporized deactivating agent is generated, or other parameter. In this regard, controller 250 is operable to actuate and deactuate the various components of apparatus 10 to effect deactivation of contaminants within defined region 12 during a deactivation cycle.

A typical deactivation cycle preferably includes a drying phase, a conditioning phase, a deactivation phase, and a destroying phase. Each phase may be limited or expanded as required to effectively deactivate contaminants within defined region 12.

When the drying phase commences, valve 222 is in the first position and controller 250 causes blower motor 226 to drive blower 224, thereby causing gas from defined region 12 to be drawn into conduit 202, through first louver 208. It is appreciated that the gas drawn into conduit 202 from defined region 12 is comprised of an atmosphere of defined region 12. The atmosphere of defined region 12 can be comprised of a variety of pure gases, mixtures of gases, water vapor, gases containing suspended particulate or moisture droplets, and the like. The atmosphere of defined region 12 can also contain the vaporous deactivating agent during various stages of the operation of apparatus 10. Therefore, the term "gas" as used herein should be understood to include the atmosphere of defined region 12.

After being drawn into conduit 202, the gas flows through apparatus 10 and is then returned to defined region 12. During the drying phase, dryer 234 removes moisture from the gas circulating through primary conduit 202 and defined region 12 as illustrated by the arrows in FIG. 1. When the gas has been dried to a sufficiently low, predetermined humidity level, the drying phase is complete. It is contemplated that the predetermined humidity level will be chosen according to the concentration of vaporous deactivating agent to be used within defined region 12 and the degree of deactivation desired. In the illustrated embodiment, destroyer 232 is not operated during the drying phase.

At the beginning of the conditioning phase, controller 250 activates valve 222 such that valve 222 is in the second position. During the conditioning phase, the gas flowing through conduit 202 bypasses catalytic destroyer 232 and dryer 234 and flows through heater 238, and vaporizer 172. Controller 250 then actuates pump motor 176, causing pump 174 to provide liquid deactivating agent to vaporizer 172. Vaporizer 172 vaporizes the liquid deactivating agent to introduce the vaporous deactivating agent into the gas flowing through vaporizer 172.

As indicated above, the liquid deactivating agent supplied to vaporizer 172 is a hydrogen peroxide solution comprised of about 35% hydrogen peroxide and about 65% water. A liquid deactivating agent solution comprised of other ratios of hydrogen peroxide and water is also contemplated. The liquid deactivating agent is vaporized within vaporizer 172 to produce vaporized hydrogen peroxide and water vapor. The vaporized hydrogen peroxide is introduced into the conduit 202 and is conveyed by the gas moving through conduit 202 into defined region 12.

During the conditioning phase, vaporized hydrogen peroxide is conveyed by the gas into defined region 12 to bring the concentration level of vaporized hydrogen peroxide up to the target concentration level in a relatively short period of time. During the conditioning phase, blower 224 causes gas to continuously circulate through apparatus 10 and defined region 12.

After the conditioning phase is completed, the deactivation phase is initiated. Valve 222 remains in the second position such that gas flowing through conduit 202 bypasses catalytic destroyer 232 and dryer 234.

During the deactivation phase, vaporizer 172 is operated to provide vaporized hydrogen peroxide. Heater 238 heats the gas entering vaporizer 172. Controller 250 monitors the signal returned by vaporous deactivating agent sensor 242 and compares that signal to the desired concentration of vaporous deactivating agent and to predetermined upper and lower limits of concentration relative to the desired concentration of vaporous deactivating agent. Controller 250 then adjusts the amount of vaporized hydrogen peroxide introduced by vaporizer 172 into the gas accordingly. Thus, vaporous deactivating agent sensor 242, controller 250, and vaporizer 172 operate as a closed-loop feedback deactivating agent control system maintaining a desired concentration of vaporized hydrogen peroxide within defined region 12. More specifically, vaporized hydrogen peroxide will degrade over time as it is transferred through conduit 202 and defined region 12 as illustrated by the arrows in FIG. 1. Therefore, supplemental vaporized hydrogen peroxide is introduced into conduit 202 by vaporizer 172 in order to maintain the desired concentration of vaporized hydrogen peroxide within the predetermined limits.

It is preferred to maintain vaporized hydrogen peroxide concentrations within the predetermined limits in order to achieve the desired degree of deactivation. As indicated above, the desired concentration of vaporous deactivating agent or the duration of the deactivation phase can vary in accordance with region parameters. The deactivation phase is continued for a predetermined period sufficient to effect the desired deactivation of contaminants within defined region 12 and items therein.

It is appreciated that apparatus 10 may remain in one location within defined region 12 throughout a deactivation cycle and then relocate to another location within defined region 12 and execute a subsequent deactivation cycle. In certain instances, apparatus 10 may move about defined region 12 during the deactivation phase, as described above, such that vaporized hydrogen peroxide is distributed throughout defined region 12.

During a "mobile" deactivation phase, system controller 250 actuates drive mechanisms 30*a*, 30*b* to move apparatus 10 about defined region 12 while the deactivation phase occurs, thereby distributing vaporous deactivating agent throughout defined region 12. In one embodiment, apparatus 10 moves about defined region 12 systematically during a moving deactivation phase, such that all areas within defined region 12 are exposed to vaporous deactivating agent.

In the illustrated embodiment, controller 250 is programmed to determine the location of apparatus 10 relative to the perimeter of defined region 12 using data provided by echolocator 246 and to store the data provided by echolocator 246. In the illustrated embodiment, system controller 250 is programmed to utilize the stored data to indicate previous locations of apparatus 10 relative to the perimeter of defined region 12. Controller 250 is also programmed to activate drive mechanisms 30*a*, 30*b* in conjunction with analysis of the location of apparatus 10 and the stored data indicating previous locations of apparatus 10. In this manner, apparatus 10 distributes vaporous deactivating agent evenly within defined region 12 during the deactivation phase. It is appreciated that the distribution of vaporous deactivating agent could be further effected by manipulation of the orientations of first louvers 208 and second louvers 216. It is also appreciated that in one embodiment, random movement of apparatus 10 during a moving deactivation phase replaces the systematic movement of apparatus 10 described above.

After the deactivation phase is completed, controller 250 causes vaporizer 172 to shut down, thereby shutting off the introduction of deactivating agent to primary conduit 202.

Next, the destroying phase, is initiated to reduce the level of the vaporized hydrogen peroxide. In this respect, controller 250 actuates catalytic destroyer 232. Controller 250 activates valve 222 such that valve 222 is moved to the first position and gas flowing through conduit 202 flows through catalytic destroyer 232 and dryer 234. Catalytic destroyer 232 is operable to destroy vaporized hydrogen peroxide flowing therethrough. Catalytic destroyer 232 converts the vaporized hydrogen peroxide into water and oxygen. Furthermore, when valve 222 is in the first position, dryer 234 is operable to remove moisture from the gas flowing through primary conduit 202.

Blower 224 continues to recirculate the gas and remaining vaporized hydrogen peroxide through defined region 12 and apparatus 10. Eventually a portion of the vaporized hydrogen peroxide will be delivered to catalytic destroyer 232 and will be broken down. The destroying phase preferably lasts for a sufficient period to allow for satisfactory reduction of vaporized hydrogen peroxide levels inside defined region 12.

System controller 250 controls the duration of the destroying phase such that the destroying phase continues until vaporous deactivating agent sensor 242 senses the predetermined threshold level of vaporized hydrogen peroxide gas in defined region 12.

In an alternate embodiment of the present invention, the destroying phase has a predetermined duration. Apparatus 10 can move about defined region 12 during the destroying phase to insure that the concentration of vaporized hydrogen peroxide throughout defined region 12 is below the predetermined threshold.

In yet another alternate embodiment, if V is greater than $V_{max}$, then apparatus 10 treats defined region 12 using multiple deactivation cycles. Apparatus 10 treats a first portion of defined region 12 using a first deactivation cycle and then treats a second portion of defined region 12 using a second deactivation cycle. It is appreciated that V may be two or more multiples of $V_{max}$. When V is two or more multiples of $V_{max}$, then defined region 12 will be treated in multiple portions where each portion is defined as a deactivation zone, wherein each deactivation zone has a volume $V_n$, that is less than $V_{max}$.

In this embodiment, apparatus 10 may move about a deactivation zone during the deactivation phase, as described above, such that vaporized hydrogen peroxide is distributed throughout the deactivation zone. It is also appreciated that apparatus 10 may remain in one location throughout a deactivation cycle and then relocate to another location in another deactivation zone to execute a subsequent deactivation cycle. In this manner, contaminants within defined region 12 are deactivated by sequential deactivation of zones.

In yet another alternate embodiment, apparatus 10 is operable to move about and define the boundaries of defined region 12 by means of a proximity sensor 262. The proximity sensor detects the boundaries of defined region 12 and objects (not shown) therein when system 12 is in near proximity or contact with the boundary or object. By way of example and not limitation, the proximity sensor is operable to mechanically or reflectively sense the location of a boundary or object. Controller 250 is programmed to store the location of the boundaries of defined area 12 and objects therein relative to apparatus 10 by a system of dead-reckoning based on the position of motors 42a, 42b. In other words, the relationship of one revolution of a motor to the distance, traveled by the associated wheel 32a, 32b is stored within system controller 250. System controller 250 thereby determines the distance traveled of each wheel 32a, 32b relative to the other at any given time. In this manner, system controller 250 determines the direction and distance traveled and the location of apparatus 10. System controller 250 utilizes stored data regarding the location of apparatus 10 within defined region 12 to develop a map of defined region 12. In this embodiment, the height of defined region 12 is stored in a predetermined data set by controller 250. System controller 250 is operable to determine the volume of defined region 12 using the stored height and data from proximity sensor 262.

In other embodiments, by way of example and not limitation, the vaporous deactivating agent may include one of the following: ozone, chlorine, a chlorine containing compound, bromine, a bromine containing compound, and a combination thereof.

The foregoing descriptions are specific embodiments of the present invention. It should be appreciated that these embodiments are described for purposes of illustration only, and that those skilled in the art may practice numerous alterations and modifications without departing from the spirit and scope of the invention. It is intended that all such modifications and alterations be included insofar as they come within the scope of the invention as claimed or the equivalents thereof.

Having described the invention, the following is claimed:

1. A method of deactivating contaminants within a defined region using a mobile deactivation apparatus movable in said defined region to dispense vaporized hydrogen peroxide therein, the method comprising:

detecting region parameters of said defined region using a sensor, said region parameters associated with dimensions of said defined region;

determining (1) a volume of said defined region from said region parameters detected by said sensor, and (2) at least one of the following operating parameters in accordance with the volume of said defined region:

(a) a duration of a deactivation phase wherein the vaporized hydrogen peroxide is dispensed within said defined region, and         (b) a desired concentration of the vaporized hydrogen peroxide within said defined region during the deactivation phase;

deactivating at least a portion of said defined region in accordance with said at least one operating parameter by controlling dispensing of the vaporized hydrogen peroxide and movement of the mobile deactivation apparatus.

2. The method of deactivating contaminants as defined in claim 1, wherein said method further comprises the step of storing said region parameters detected by said sensor.

3. The method of deactivating contaminants as defined in claim 1, wherein said sensor uses echolocation to detect said region parameters.

4. The method of deactivating contaminants within a defined region as defined in claim 1, including the step of:

comparing the volume of said defined region to a predetermined maximum volume to determine whether said mobile deactivation apparatus should remain stationary or move within said defined region while dispensing said vaporized hydrogen peroxide.

5. The method of deactivating contaminants as defined in claim 1, including the step of:

dispensing said vaporized hydrogen peroxide while said mobile deactivation apparatus is stationary within said defined region.

6. The method of deactivating biological contaminates as defined in claim 1, including the step of:

dispensing said vaporized hydrogen peroxide while said mobile deactivation apparatus is moving within said defined region.

7. The method of deactivating contaminants as defined in claim 1, including the steps of:

moving said mobile deactivation apparatus about said defined region;

storing data regarding a perimeter of said defined region;

dividing the defined region into a plurality of zones based on said stored data; and     deactivating at least a portion of at least one of said zones.

8. The method of deactivating contaminants as defined in claim 1, wherein said method further comprises:

sensing a concentration of the vaporized hydrogen peroxide within said defined region; and     providing data indicative of the concentration of said vaporized hydrogen peroxide to a system controller for controlling operation of said mobile deactivation apparatus.

9. The method of deactivating contaminants as defined in claim 8, wherein said step of deactivating at least a portion of said defined region includes the step of:

dispensing said vaporized hydrogen peroxide such that said concentration of said vaporized hydrogen peroxide is maintained within a predetermined range.

10. The method of deactivating contaminants as defined in claim 8, includes the step of:

wirelessly communicating said data indicative of said concentration of said vaporized hydrogen peroxide to a base station located outside of said defined region.

11. The method of deactivating contaminants as defined in claim 1, wherein said method further comprises:
detecting a location of a boundary of said defined region or a location of an object disposed within said defined region.

12. The method of deactivating contaminants as defined in claim 1, wherein said method further comprises:
determining whether said mobile deactivation apparatus should be mobile while dispensing said vaporized hydrogen peroxide based upon the volume of said defined region.

13. The method of deactivating contaminants as defined in claim 1, wherein said method further comprises:
determining the volume (V) of said defined region according to equation V=HA where:
H is a height of said defined region, and
A is an area of said defined region.

14. The method of deactivating contaminants as defined in claim 13, wherein said method further comprises:
storing a data set for determining the height H of said defined region.

15. The method of deactivating contaminants as defined in claim 13, wherein said method further comprises:
determining the height H of said defined region using said region parameters detected by said sensor.

16. The method of deactivating contaminants as defined in claim 13, wherein said method further comprises:
determining an area A of said defined region using said region parameters detected by said sensor.

17. The method of deactivating contaminants as defined in claim 1, wherein said method further comprises:
running multiple deactivation phases for dispensing said vaporized hydrogen peroxide within said region, if the volume of said defined region exceeds a predetermined maximum volume ($V_{MAX}$).

18. The method of deactivating contaminants as defined in claim 1, wherein said method further comprises:
determining a location of a perimeter of said defined region relative to a current location of said mobile deactivation apparatus within said defined region.

* * * * *